United States Patent
Wagenknecht

[11] Patent Number: 5,167,661
[45] Date of Patent: Dec. 1, 1992

[54] DEVICE FOR ARTICULATION AND RELATIVE LOCKING OF TWO PIECES

[75] Inventor: Marcel H. Wagenknecht, Le Lignon, Switzerland

[73] Assignee: Jaquet Orthopedie S.A., Geneva, Switzerland

[21] Appl. No.: 588,797

[22] Filed: Sep. 27, 1990

[51] Int. Cl.⁵ ............................................. A61B 17/60
[52] U.S. Cl. .................................... 606/54; 606/59; 403/55; 403/165
[58] Field of Search ............. 403/53, 59, 55, 90, 403/103, 104, 164, 165, 78; 606/54–59

[56] References Cited

U.S. PATENT DOCUMENTS

| 361,683 | 4/1887 | Eckhart | 403/165 X |
| 2,323,624 | 7/1943 | Schall | 403/53 X |
| 2,887,329 | 5/1959 | Blakely | 285/168 |
| 4,475,546 | 10/1984 | Patton | 606/57 |
| 4,561,797 | 12/1985 | Aldridge | 403/164 X |
| 4,669,907 | 6/1987 | Patton | 403/165 X |
| 4,723,804 | 2/1988 | Gatens | 403/165 X |
| 4,988,349 | 1/1991 | Pennig | 606/59 X |

FOREIGN PATENT DOCUMENTS

| 807720 | 7/1949 | Fed. Rep. of Germany . |
| 927370 | 5/1946 | France . |
| 1123300 | 3/1955 | France . |
| 2346594 | 1/1976 | France . |
| 245092 | 7/1947 | Switzerland . |
| 303453 | 5/1952 | Switzerland . |
| 625982 | 7/1949 | United Kingdom ........ 403/53 |

Primary Examiner—Robert A. Hafer
Assistant Examiner—Kevin G. Rooney
Attorney, Agent, or Firm—Peter C. Richardson; Lawrence C. Akers; Elizabeth O. Slade

[57] ABSTRACT

This articulation device makes it possible to position a first elongated piece 20, which is capable of being pivoted through 360° according to the arrow A, and a second piece 30, which is capable of swivelling about the shaft 40 according to the arrow B. These pieces are made integral with a U-shaped support 10, in relation to which they can be locked by shoes 60 and 70 which are held in position by a single securing screw 50. The pieces 20 and 30 can be connected to elements which are to be positioned, such as pins or connection rods which form part of an orthopaedic external fixing appliance consisting of pins inserted into bone fragments and of an external frame with connection rods.

10 Claims, 2 Drawing Sheets

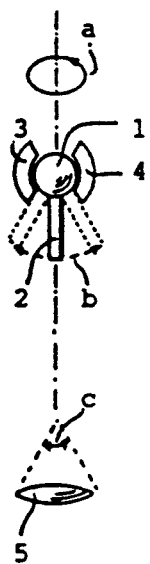
Fig. 1
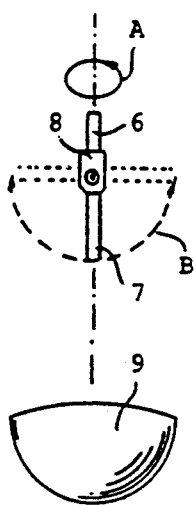
Fig. 2
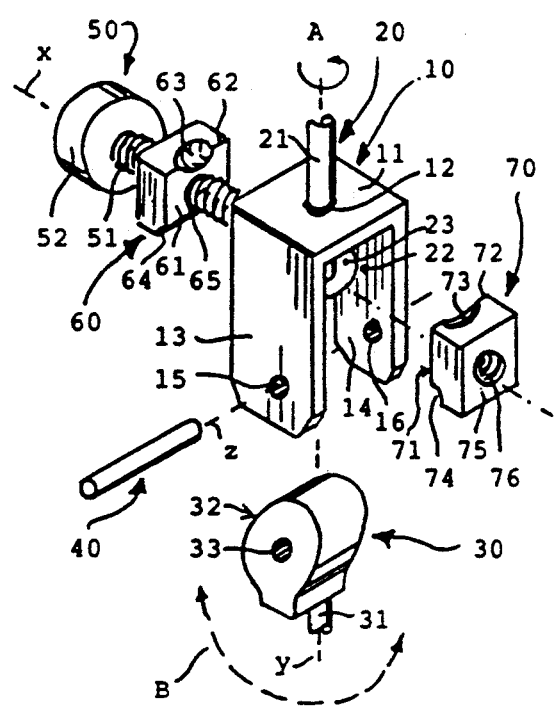
Fig. 3
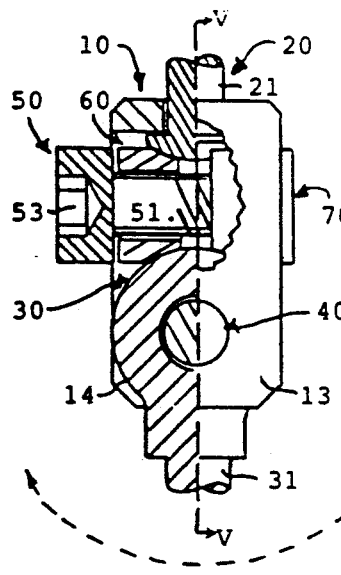
Fig. 4
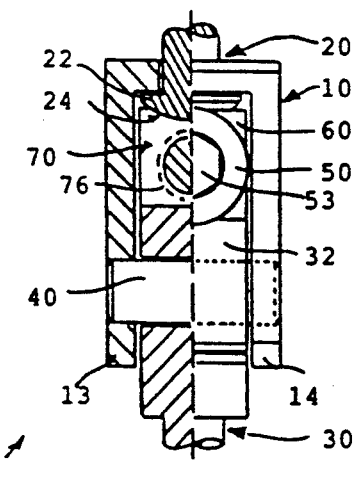
Fig. 5
Fig. 6
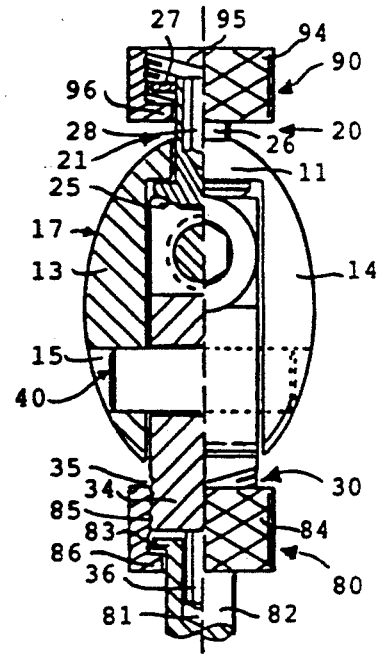

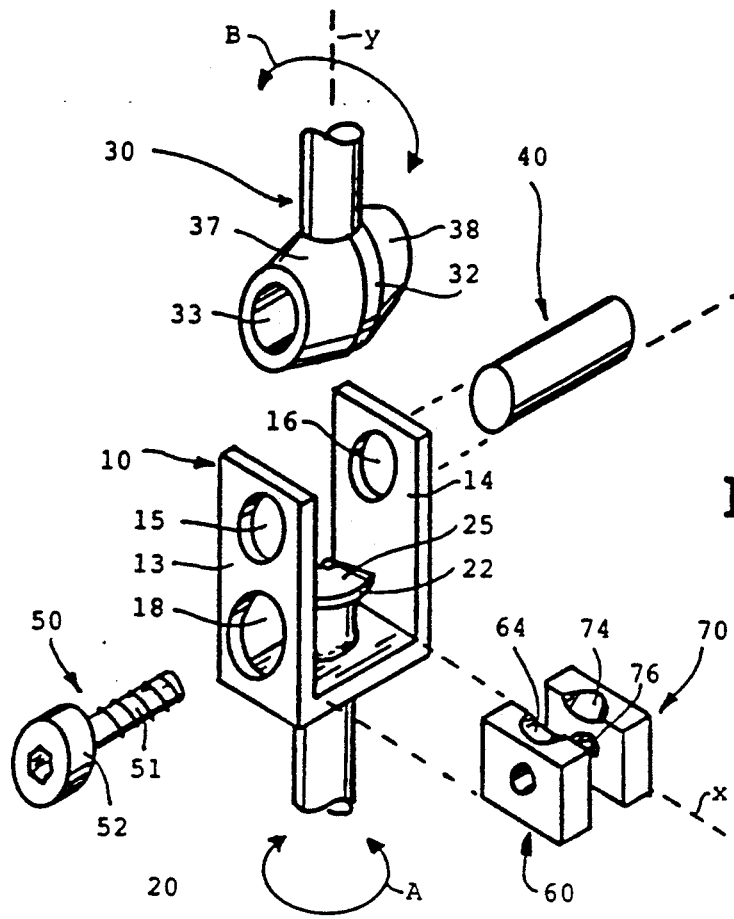
Fig. 7
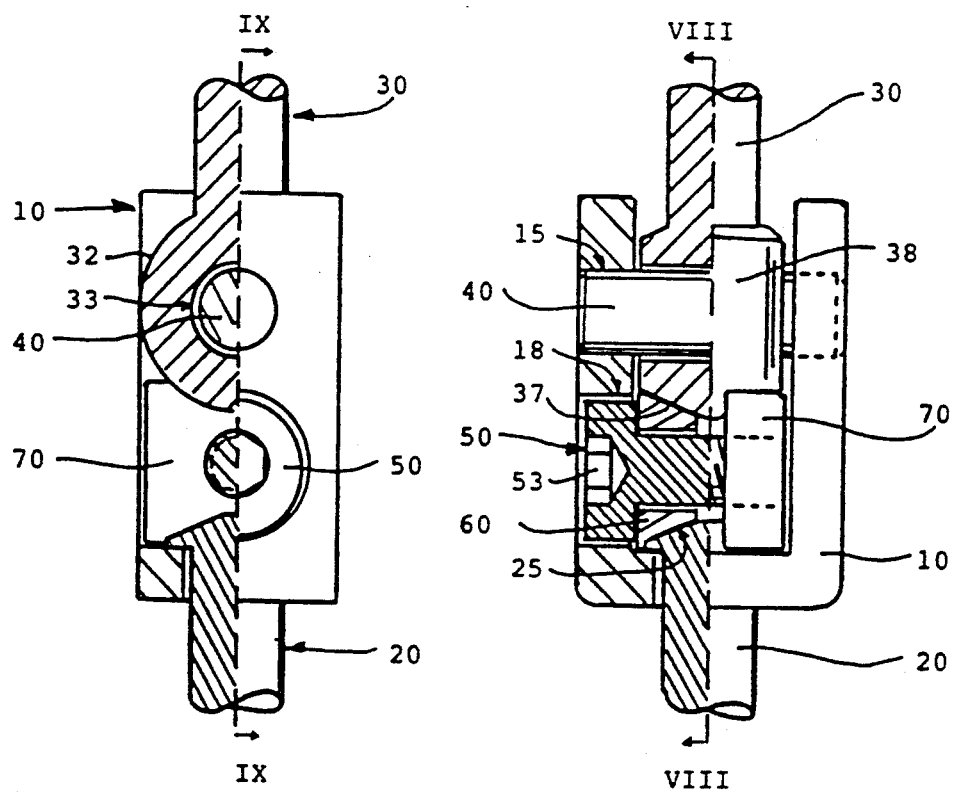
Fig. 8
Fig. 9

DEVICE FOR ARTICULATION AND RELATIVE LOCKING OF TWO PIECES

The present invention lies within the field of mechanics and relates to a device for articulation between two pieces which are intended to be locked in a specific position, designed especially for use in an external surgical fixing appliance.

When two pieces are to be positioned with more than one degree of angular freedom, either systems which permit separate adjustment along several axes or universal joints are used. In the case of the former, locking is effected by a number of securing systems which corresponds to that of the axes of rotation, which implies several securing operations. In the second case, ball and socket joints are used which can be locked by one single securing operation but which have the disadvantage of limiting the positioning possibilities as a result of the presence of the jaws which surround the spherical part to be held in position.

The present invention aims to overcome these disadvantages and consequently relates to a device for articulation and relative locking of two elongated pieces, characterized in that it comprises:

a) a U-shaped support capable of receiving the said pieces, b) a first piece which is pivotable about its axis, c) a second piece which is swivellable about a shaft arranged perpendicularly to the said axis of the first piece, and d) means of locking arranged on either side of the said first and second pieces, on a single securing shaft.

In a preferred embodiment, the U-shaped support comprises a central part with a central passage for the first piece and two wings which have openings which are situated on a common axis and capable of receiving the securing shaft.

According to a first alternative, the securing shaft is arranged parallel to the wings, whereas in a second alternative it is arranged between the wings, perpendicularly to the latter.

The invention also extends to an application of a device as described in an external fixing appliance intended to hold in position pins which are inserted into bone fragments. In known external fixing appliances, the pins are in general inserted into the bone using a template which corresponds to a specific pin support, which is tantamount to saying that the insertion of the pins must be adapted to the geometry of the fixing appliance used.

By using devices for articulation according to the invention, there is free scope to insert each pin into the bone fragment to be held in position according to the configuration of the fracture on the one hand and according to the anatomical areas which are favourable to insertion on the other, avoiding the perforation of arteries, nerves or ligaments. The pins, which are thus inserted along very variable axes, are connected to the external fixing appliance, with articulations according to the invention interposed, which permit their accurate positioning in relation to the fixing appliance.

The attached drawing shows, by way of non-limitative examples, alternative embodiments of the subject of the present invention.

FIG. 1 is a schematic view of a conventional ball and socket joint and of the extent of the movement which it allows.

FIG. 2 is a similar view to that in FIG. 1, with an articulation according to the invention.

FIG. 3 is an exploded perspective view of the principal components of the proposed articulation, in a first embodiment.

FIG. 4 is, on its left side, a cross-section of the articulation, along the orthonormed axes x and y in FIG. 3 and, on its right side, a lateral view perpendicular to the axis z, partially cut away.

FIG. 5 is, on its left side, a cross-section of the articulation, along V—V in FIG. 4 and, on its right side, a lateral view perpendicular to the axis x.

FIG. 6 is a representation similar to that in FIG. 5, in an alternative embodiment which proposes an application of the articulation according to the invention.

FIG. 7 is an exploded perspective view of a second embodiment of the articulation.

FIGS. 8 and 9 correspond, with regard to this second embodiment, to FIGS. 4 and 5.

With reference to FIG. 1, there is in the upper part of the drawing a conventional ball and socket joint which comprises a spherical part 1, which is extended by a rod 2, and a pair of jaws 3 and 4. The rod 2 can be pivoted through 360° according to the arrow a, but the swivelling according to the arrow b is limited by the presence of the jaws 3 and 4 in such a manner that the end of the rod 2 can only describe the spherical cap 5 shown in the lower part of FIG. 1, in which the angle c is in general limited to approximately 60°.

The new articulation proposed here and shown schematically in FIG. 2 comprises a rod 6 and a rod 7 arranged on either side of a housing 8. In addition to the possibility of pivoting the rod 6 through 360° according to the arrow A, as in the previous case, the rod 7 can be swung according to the arrows B through an angle of 90° on each side of the vertical axis in such a manner that the end of the rod 7 can describe the hemisphere 9 shown in the lower part of FIG. 2.

The principal components of the subject of the invention are shown in the general view in FIG. 3 and comprise a support in the form of a double right-angle 10, a first articulation arm 20 along the axis y of an orthonormed system, a second articulation arm 30 which can be aligned on the axis of the first and which is mounted pivotably on a shaft 40 which is arranged along the axis z of the drawing. A securing screw 50, arranged along the axis x, makes it possible to hold two shoes 60 and 70 in position.

The support in the form of a double right-angle 10 is more specifically constituted by a central part 11, which has a central passage 12 for the first articulation arm 20, and by two wings 13 and 14 which have openings 15 and 16 which are situated on a common axis and in which the shaft 40 is fixed. The internal faces of the central part 11 and of the wings 13 and 14 are plane.

The first articulation arm 20 comprises a shaft 21 which passes through the central passage 12 and a head 22 which has an internal flat side 23 which is intended to bear against the inside of the central part 11 of the support 10. Externally the head 22 has a special shape which will be described in detail later. The shaft 21 can be rotated in relation to the support 10 according to the arrow A.

The second articulation arm 30 comprises a shaft 31 which extends perpendicularly to a body 32 which has the general shape of a cylinder and a central passage 33. The length of the cylinder 32 is such that it can be introduced with clearance between the wings 13 and 14, and the diameter of the central passage 33 allows the pivoting of the articulation arm 30 on the shaft 40.

This shaft 40 is fixed, by crimping for example, in the openings 15 and 16 which are formed at the same height in the wings 13 and 14. The shaft 40 passes freely through the central passage 33, so as to permit the swinging according to the arrow B of the second articulation arm 30.

The securing screw 50 is intended to lock the whole in the desired position. It consists of a threaded rod 51 and a cylindrical head 52.

The shoes 60 and 70 are constituted by blocks with a generally parallelepipedal shape, the opposing faces 61, 71 of which have on one edge 62, 72 a hollow 63, 73, which corresponds to the external shape of the head 22, and on the opposite edge a cylindrical recess 64, 74 which is intended to interact with the cylindrical body 32. Each shoe 60, 70 also has an opening 65, 75 which is preferably situated in the centre of the block. The central opening 65 is intended to allow free passage of the threaded rod 51 of the securing screw 50, whereas the central opening 75 is provided with an inside thread 76 which is intended to interact with the threaded rod 51 in order to provide for the securing of the whole.

Provision can also be made to replace the inside thread 76 with an opening into which the threaded rod 51 passes freely before engaging in a nut which is not shown in the drawing.

With reference to FIGS. 4 and 5, the assembly of the elements mentioned above can be seen. Although the shafts 21 and 31 are shown as aligned, it is to be borne in mind that the articulation arm 30 can be swung about the axis 40 according to the arrow B, whereas the arm 20 permits an orientation of 360° about the shaft 21.

More specifically observable is the external shape of the head 22 which is a spherical cap 24 which is intended to interact with the hollows 63 and 73 of the shoes 60 and 70.

It can also be observed that the head 52 of the screw 50 has a hexagonal opening 53 which is intended to interact with a hexagonal securing key in order to rotate the threaded rod 51 in the corresponding inside thread 76 of the shoe 70.

In the alternative proposed in FIG. 6, the ellipsoid external shape 17 of the support in the form of a double right-angle 10 can be observed. It can also be observed that the head 22 has a truncated part 25 which is intended to interact with corresponding truncated hollows 63, 73 of the shoes 60 and 70.

The articulation in FIG. 6 is shown with connectors 80 and 90 which provide for the assembly of the former in a whole which is not shown in the drawing.

The connector 80 provides for the connection to the articulation arm 30. To this end, the shaft 34 has a thread 35 and ends in a hexagonal rod 36 which is intended to interact with a corresponding opening 81 in the connection piece 82 which also has a collar 83. The connector 80 is fixed by a knurled ring 84 which has an inside thread 85, which is intended to interact with the thread 35, and a support shoulder 86 for the collar 83.

The connector 90 provides in a similar manner for the connection of the articulation arm 20, the shaft 26 of which has a washer 27 and a central hexagonal opening 28 which is intended to receive a rod of corresponding shape of a connection piece, which is not shown in the drawing. The connector 90 is fixed by a knurled ring 94 which has an inside thread 95, which is intended to interact with a thread of the connection piece, and a support shoulder 96 for the washer 27.

In the second embodiment shown in FIGS. 7 to 9, the majority of the components described previously can be seen with the same reference numbers. It is simply to be observed that, in FIGS. 7 to 9, the articulation arm 20, intended to pivot about its axis, is shown at the bottom whereas the articulation arm 30, intended to pivot about the shaft 40, is shown at the top of the figures.

This second embodiment differs in that the shaft 40 and the securing screw 50 are in the same plane instead of being perpendicular to one another as previously.

To this end, the wing 13 of the U-shaped support 10 has, in addition to the opening 15 intended for fixing the shaft 40, an opening 18 which is dimensioned to allow free passage of the head 52 of the securing screw 50.

The articulation arm 20 has a head 22 which has a truncated part 25 which is intended to interact with corresponding hollows of the shoes 60 and 70.

The articulation arm 30 has as previously a body 32 with the general shape of a cylinder and a central passage 33 which provides for articulation on the shaft 40. Externally the body 32 has two truncated ends 37 and 38 which are intended to interact with the recesses 64 and 74 of the shoes 60 and 70.

The majority of the pieces mentioned until now are metal and in general made of stainless steel; only the U-shaped support 10 can be made of a light alloy. The majority of the angular edges are chamfered, although this is not shown rigorously in the drawing.

In order to increase the gripping qualities of the articulation, provision can be made to make the shoes 60 and 70 from tungsten carbide or to treat the contacting surfaces of the screw head 22, of the shoes 60 and 70 and of the cylinder 32 by machining shallow reliefs (of several hundredths of a millimeter for an articulation of an order of size of several centimeters) onto them or by applying a surface treatment by granulating.

Assembly of the elements which form the articulation shown in FIGS. 3 to 5 is carried out by introducing the first articulation arm 20 into the opening 12 formed in the central part of the support 10. Then the second articulation arm 30 is fixed between the wings 13 and 14 by means of the shaft 40, which is crimped in the openings 15 and 16, and the shoes 60 and 70 are threaded onto the securing screw 50 on either side of the head 22 and the body 32. Once the articulation is assembled, the articulation arms 20 and 30 can be rotated into the desired position before the screw 50 is secured in the shoe 70 in order to hold the head 22 and the cylindrical body 32 in the appropriate position.

In the locked position, the internal flat side 23 of the head 22 is held in position against the internal face of the central part 11 of the support 10 whereas the external part of the head 22 rests in the hollows 63 and 73 of the shoes 60 and 70, thus locking the first articulation arm 20. The cylindrical recesses 64 and 74 bear against the surface of the cylindrical body 32, locking the second articulation arm 30.

It goes without saying that, without leaving the scope of the invention, the internal flat side 23 of the head can be replaced with a spherical or truncated surface which is intended to interact with a hollow or a protuberance of corresponding shape formed in the internal face of the central part 11.

As has already been mentioned, the articulation in FIG. 6 is more specifically designed for an external fixing appliance of pins inserted into bone parts, more specifically in traumatology. This device with an ellipsoid housing has the advantage of avoiding angles and edges which may impede the patient and above all it makes it possible to freely insert the pins in preferred areas surrounding the bone fragment to be held in position, irrespective of the components of the fixing appliance itself, since the pins can be positioned in relation to these by interposing positioning devices according to the invention. The connectors 80 and 90 are then mounted at the two ends of the device, as shown in FIG. 6.

It can be observed that connection is effected by means of a system which avoids any rotation of the rods which are put into the ends of the described device since the hexagonal rod 36 interacts with a corresponding opening 81 in the piece to be connected 82, in the same way as the central hexagonal opening 28 receives a piece to be connected of corresponding shape.

It is of course possible to replace these hexagonal pieces and openings with any other component which avoids rotation and is known to the expert, such as an element which consists of flat sides, wedges or others.

Assembly of the elements which form the articulation shown in FIGS. 7 to 9 is carried out by introducing the first articulation arm 20 into the opening 12 of the U-shaped support 10 in such a manner that its head 22 rests on the central part 11. The shoes 60 and 70 are positioned as shown in FIG. 9. The body 32 of the second articulation arm 30 is introduced between the wings 13 and 14 and fixed by insertion of the shaft 40 into the openings 15 and 16.

The screw 50 is then introduced and the threaded rod 51 engages with the inside thread 76 whereas the head 52 is introduced into the opening 18 formed in the U-shaped support 10. Securing of the screw 50 brings the shoes 60 and 70 towards one another in such a manner that:

the hollows 63 and 73 bear against the truncated part 25 of the head 22, in order to avoid rotation of the first articulation arm 20 according to the arrow A, and the recesses 64 and 74 bear against the truncated ends 37 and 38 of the cylindrical body 32, thus making it possible to lock the second articulation arm 30 in the required angular position.

This second embodiment has the advantage that the shoes 60 and 70 remain in position when the screw 50 is withdrawn.

I claim:

1. An articulation device which can be locked in any selected position, said device comprising:
   (a) a first elongated piece (20) having a longitudinal axis and being pivotable about said longitudinal axis;
   (b) a second elongated piece (30) which is swivellable about a shaft (40) arranged perpendicular to said longitudinal axis of said first elongated piece;
   (c) a U-shaped support (10) capable of receiving said first elongated piece (20) and said second elongated piece (30), wherein said U-shaped support (10) comprises:
      (1) a central part (11) with a central passage (12) for said first elongated piece (20) and
      (2) a first wing (13) and a second wing (14) which have located therein respectively a first opening (15) and a second opening (16) situated on a common axis and capable of receiving said shaft (40); and
   (d) a locking means (60, 70) for locking into a selected position said first elongated piece (20) and said second elongated piece (30), and wherein said first elongated piece (20) has a head (22) which can cooperate with said support (10) and with said locking means (60, 70).

2. An articulation device according to claim 1, wherein said head (22) has an external surface in a shape selected from the group consisting of a spherical cap (24) and a truncated shape (25).

3. An articulation device according to claim 2 wherein said locking means (60, 70) comprises a first opposing face (61) and a second opposing face (71) with a first hollow (63) and a second hollow (73) located respectively therein and into which said head (22) can fit.

4. An articulation device according to claim 1, wherein said second elongated piece (30) has a part (32) with a shape of a cylinder and arranged perpendicular to said axis of said second elongated piece (30) and operable in cooperation with said locking means (60, 70).

5. An articulation device according to claim 4, wherein said part (32) has a first truncated end (37) and a second truncated end (38) which are intended to cooperate with said locking means (60, 70).

6. An articulation device according to claim 5, wherein said part (32) can be arranged between said first wing (13) and said second wing (14) of said support (10) and has a central passage (33) capable of receiving with clearance said shaft (40).

7. An articulation device according to claim 5, wherein said locking means (60, 70) has located on said first opposing face (61) and on said second opposing face (71) a hollow (63, 73) which fits with a portion of said second elongated piece (30).

8. An articulation device according to claim 1, wherein said locking means (60, 70) comprises a first opposing face (61) and a second opposing face (71) and wherein said locking means (60, 70) has passages (65, 75) which are perpendicular to said first opposing face (61) and to said second opposing face (71) and which are capable of receiving said securing shaft (50) and wherein an item selected from the group consisting of said first wing (13) and said second wing (14) has an opening (18) located therein through which a securing shaft (50) can pass and including also said securing shaft (50) and wherein said locking means (60, 70) is located on said securing shaft (50).

9. An articulation device according to claim 8, wherein said securing shaft (50) comprises a screw having a threaded part 51 which can pass freely through said passage (65) and engage with an inner thread (76) located within said passage (75).

10. An articulation device according to claim 8, wherein said securing shaft (50) comprises a screw having a threaded part (51) which can pass freely through said first passage (65) and said second passage (75) and which can engage with a nut.

* * * * *